United States Patent
Bayer et al.

(10) Patent No.: US 11,951,024 B2
(45) Date of Patent: Apr. 9, 2024

(54) X-RAY MARKERS FOR SCAFFOLDS

(71) Applicant: BIOTRONIK AG, Buelach (CH)

(72) Inventors: Ullrich Bayer, Bad Doberan (DE); Fabian Risch, Schaffhausen (CH); Johannes Riedmueller, Nuremberg (DE); Bodo Quint, Dettinghofen (DE)

(73) Assignee: BIOTRONIK AG, Buelach (CH)

( * ) Notice: Subject to any disclaimer, the term of this patent is extended or adjusted under 35 U.S.C. 154(b) by 940 days.

(21) Appl. No.: 16/475,544

(22) PCT Filed: Jan. 8, 2018

(86) PCT No.: PCT/EP2018/050345
§ 371 (c)(1),
(2) Date: Jul. 2, 2019

(87) PCT Pub. No.: WO2018/130489
PCT Pub. Date: Jul. 19, 2018

(65) Prior Publication Data
US 2019/0336310 A1    Nov. 7, 2019

(30) Foreign Application Priority Data

Jan. 11, 2017    (EP) ..................................... 17150973

(51) Int. Cl.
*A61F 2/82* (2013.01)
*A61B 90/00* (2016.01)
*B23P 15/00* (2006.01)

(52) U.S. Cl.
CPC ................ *A61F 2/82* (2013.01); *A61B 90/39* (2016.02); *B23P 15/00* (2013.01); *A61B 2090/3966* (2016.02); *A61F 2250/0071* (2013.01); *A61F 2250/0098* (2013.01)

(58) Field of Classification Search
CPC ... A61F 2/82; A61B 90/39; A61B 2090/3966; B23P 15/00; C25F 3/16; B23K 5/00
See application file for complete search history.

(56) References Cited

U.S. PATENT DOCUMENTS

| | | | |
|---|---|---|---|
| 8,464,927 B2 * | 6/2013 | Pinchot | B21D 33/00 422/600 |
| 8,721,709 B2 | 5/2014 | Schlun et al. | |
| 8,992,600 B2 | 3/2015 | Goetzen et al. | |
| 10,272,183 B2 | 4/2019 | Bayer et al. | |
| 2010/0131052 A1 * | 5/2010 | Kappelt | A61L 31/148 623/1.46 |
| 2014/0014530 A1 * | 1/2014 | Lin | A61F 2/86 205/660 |

FOREIGN PATENT DOCUMENTS

| | | | | |
|---|---|---|---|---|
| DE | 102013020689 B3 * | 2/2015 | | A61B 90/39 |
| DE | 102013020689 B3 | 2/2015 | | |
| EP | 2399619 A2 | 12/2011 | | |

(Continued)

*Primary Examiner* — Dah-Wei D. Yuan
*Assistant Examiner* — Andrew J Bowman
(74) *Attorney, Agent, or Firm* — Laurence A. Greenberg; Werner H. Stemer; Ralph E. Locher

(57) ABSTRACT

A method for producing x-ray markers. During the process, a predetermined breaking point is severed in order to detach x-ray markers from part of a material layer. There is also described an x-ray marker, a medical implant, and a semi-finished product.

11 Claims, 10 Drawing Sheets

(56) References Cited

FOREIGN PATENT DOCUMENTS

| EP | 2457601 | A2 | 5/2012 | | |
|----|---------|----|--------|---|---|
| WO | 9737616 | A2 | 10/1997 | | |
| WO | WO97/37616 | * | 10/1997 | ............... | A61F 2/06 |
| WO | 0215820 | A2 | 2/2002 | | |
| WO | WO-0215820 | A2 * | 2/2002 | ............... | A61F 2/89 |
| WO | 2009030748 | A3 | 3/2009 | | |
| WO | WO-2009030748 | A2 * | 3/2009 | ............... | A61F 2/86 |

* cited by examiner

X-RAY MARKERS FOR SCAFFOLDS

BACKGROUND OF THE INVENTION

Field of the Invention

The invention relates to a method for producing x-ray markers, and also to a medical implant comprising at least one such x-ray marker. An implant of this type can have, for example, a framework (also referred to as a scaffold), in particular a stent framework, which is preferably degradable, i.e. after implantation disintegrates in a defined manner in the body of the patient over a specific period of time.

EP 2 457 601 discloses composite markers, which are material combinations of metal marker particles and polymer adhesives. The mass fraction of x-ray-absorbing particles in the composite decisively determines the radiopacity. However, the fraction of said particles cannot be significantly higher than 90% by weight. At higher fractions the mixture is already so viscous in the uncured state that processing, such as injection into eyelets, is no longer possible. Since, on account of the density differences between polymer adhesives ($\rho<2$ g/cm$^3$) and x-ray-absorbing metals such as Ta ($\rho>16$ g/cm$^3$), the volume ratios are precisely the opposite of the mass ratios, a further optimisation of this technology is finite. Even if it were possible to introduce 95% by weight of x-ray-absorbing particles into a polymer-containing composite and to introduce this also in a defined manner into an eyelet, it would not be possible to achieve radiopacity equal to that of a solid x-ray marker on account of the resultant density of the composite.

In addition, the simple adhesive bonding of solid markers into the eyelets of absorbable scaffolds prevents the formation of corrosion-accelerating local elements only when the adhesive ensures a permanent local separation between marker and scaffold during the entire degradation process, which usually can be achieved only with greater effort. Corrosion-accelerating local elements form when chemically noble and chemically base metals or alloys are in direct electrical contact with one another without interfaces.

EP 2 399 619 also discloses solid markers sheathed by foreign metals. In this variant the risk of local element formation is considerably reduced, however the technical production effort is high here as well.

SUMMARY OF THE INVENTION

On this basis, the object of the present invention lies in providing a method for producing x-ray markers, which method or marker allows an improved handling of the x-ray marker during production.

In particular, a method is to be provided by means of which x-ray markers can be produced in high quantity with minimal preparative effort.

The x-ray marker should preferably also be arrangeable as close as possible to a metal framework, in particular a stent framework, which is hardly radiopaque and in particular is degradable, without any interactions and the associated corrosion effects between the materials on either side.

This should preferably also be ensured when degradation effects displace the original geometric positions of both components relative to one another - in particular in spite of a polymer adhesive as intermediate medium - and an integral bonding between the x-ray marker and the scaffold cannot be ruled out.

This object is achieved by a method having the features described herein and also by an x-ray marker having the features described herein. Advantageous embodiments of these aspects of the invention are specified in the corresponding dependent claims and will be described hereinafter. Further aspects of the invention will also be described hereinafter.

In the method according to the invention for producing x-ray markers, it is proposed that at least one material layer is provided, wherein at least one region of the material layer forming the x-ray marker to be produced is pre-cut such that said region is connected to parts of the material layer surrounding said region (in particular merely) via at least one web extended along an extension direction, which web forms a predetermined breaking point. Due to the connection via a web to the material layer, the x-ray marker is initially prevented from breaking off prematurely from the material layer.

Furthermore, the method is proposed so that the at least one predetermined breaking point is arranged in a section of the region (said section being formed in particular by the pre-cutting), such that the at least one predetermined breaking point lies further inward in the extension direction of the web (i.e. is closer to the centre of the region) than two outer edge portions of the region, between which the section lies, and wherein the at least one predetermined breaking point is severed in order to release the x-ray marker from said part of the material layer.

In other words, the at least one predetermined breaking point is arranged offset inwardly towards the core of the region or x-ray marker. Here, the core by way of example can be the centre of mass of the x-ray marker. Due to the arrangement of the at least one predetermined breaking point further inwardly compared to the other outer edges of the x-ray marker, metal-metal contact between the predetermined breaking point and for example the body of an implant and especially a stent strut is practically ruled out. As a result of this feature, the formation of corrosion-accelerating local elements can therefore be eliminated and ruled out.

In accordance with the method proposed herein and the x-ray marker proposed herein, the x-ray marker can be connected in the material layer to at least one web in the form of a predetermined breaking point. However, it can also be necessary for more than one predetermined breaking point to be present between the material layer and x-ray marker. It is therefore part of the present proposal that the x-ray marker is connected to the material layer via one, two, three, four, five or, if necessary and expedient, also more predetermined breaking points in the form of webs, as described herein. By way of example, it has been found that an embodiment with two or more predetermined breaking points provides the advantage of a simpler handling during the process of introducing the marker into the eyelet. By way of example, two opposing symmetrically arranged predetermined breaking points can thus constitute tapers of the x-ray marker. During the subsequent process of marker assembly, specially manufactured handling devices can engage in these tapers and can thus ensure a simpler assembly process. These handling devices can be micro-tweezers or micro-tongs, for example. Furthermore, due to the inward contact face between marker and handling device, is also ensured that potential damage to the marker caused by the handling lies at a point that is not critical for contact corrosion. Such a handling, in addition, can also be carried out when the inward predetermined breaking points do not lie exactly opposite one another, but are arranged offset from one another at a sufficiently large angle, for example as in the case of three predetermined breaking points distanced by 120°.

In the sense of the invention, "pre-cutting" means in particular that a gap surrounding the region and severing the material layer in part is produced and is interrupted at least by the at least one said web. In this respect, the term pre-cutting conveys the idea that the region that will form the x-ray marker, or the x-ray marker itself, is not broken off fully from the material layer, and instead is still connected thereto (via the at least one web with predetermined breaking point).

On account of the connection according to the invention of the x-ray marker to the material layer, the handling of the individual x-ray marker is improved and protection thereof is facilitated. In particular, the mechanical strength of the at least one predetermined breaking point is such that a sufficient transport and storage capability is attained without the marker breaking off prematurely. In that it is possible to process a great number of x-ray markers simultaneously. Depending on the size of the material layer the herein suggested method facilitates to simultaneous production of hundreds, if not thousands of x-ray markers. As a result an enormous number of x-ray markers can be produces exhibiting the exact same properties due to the simultaneous production. Moreover, the herein suggested method is efficient and elegant as well in that the above outlined great number of x-ray markers can be disconnected from material layer simultaneously as well rendering the production of such a large number of x-ray markers extremely economical.

The at least one material layer, in accordance with an embodiment of the invention, is in particular a flat, preferably planar material layer, of which the thickness is preferably significantly smaller than the extent of the material layer perpendicularly to the direction of the thickness of the material layer. Accordingly, the x-ray marker also has a planar form, wherein a thickness of the x-ray marker is preferably likewise significantly smaller than an extent of the x-ray marker/region perpendicular to the direction of thickness. In a further embodiment the at least one material layer can be in the form of a tube. Also the tube is supposed to have a thickness significantly smaller than the circumference of the tube. Accordingly, the x-ray marker also has a slightly curved form, wherein a thickness of the x-ray marker is preferably likewise significantly smaller than an extent of the x-ray marker/region perpendicular to the direction of thickness. Cutting from a tube in order to produce the x-ray markers is advantageous in that the the volume of the marker is slightly more compact and is thereby better x-ray visible. Furthermore, due to the curved form the edges of the marker do better adapt to the form of the eyelet on the round stent resulting the edges to lie more inwardly in the eyelet and extent less or not at all from the eyelet. Moreover, the surface of the marker is increased resulting a stronger adhesion to the stent when glued on it.

In accordance with a preferred embodiment of the method according to the invention, said pre-cutting is performed by means of laser light (here, the laser light or an appropriate laser light beam can, for example, run over the line to be cut or the gap to be cut, or the material layer is moved relative to a fixedly oriented laser beam). Other suitable methods for pre-cutting the x-ray marker/region are water jet cutting or also punching. In particular, pre-cutting by means of laser light has the advantage that large quantities can be pre-cut very quickly with high precision.

It is also proposed in accordance with a preferred embodiment of the method according to the invention that the at least one material layer is a metal foil or a metal foil composite consisting of a number of layers or a tube or tube of a composite material, which in particular is manufactured from one of the following radiopaque materials or comprises one of the following materials: tungsten, tantalum, gold, platinum, iridium, or alloys of the aforementioned materials, such as a platinum-iridium alloy.

In accordance with a preferred embodiment of the method according to the invention, provision is also made so that the web width perpendicularly to the extension direction of the web lies in the range of from 1 µm to 20 µm, and preferably in the range of from 2 to 10 µm, and in particular is 5 µm. Such a web width is in particular advantageous in respect of a use of the x-ray marker for the visualisation of implants that are the size of vessel supports, since it is possible to prevent the x-ray marker from breaking off prematurely from the material layer during the procedure. This web width also has the advantage that a desired oxidising through the web during the passivation of the x-ray marker can be quickly achieved, whereby the method can be carried out more quickly.

In accordance with a preferred embodiment of the method according to the invention, provision is also made so that, when pre-cutting, a gap running around the region is produced (see also above), which gap preferably has a width ranging from 10 µm to 100 µm, preferably ranging from 20 to 60 µm. The advantage of such a gap lies in the fact that the material layer can be cut through in a reliable manner, whilst the material loss is kept low. Furthermore, said gap is interrupted in accordance with one embodiment merely by the at least one said web.

Provision is also made in accordance with a preferred embodiment of the method according to the invention so that the region or the x-ray marker is formed in an elongate manner and extends here along a longitudinal axis. Said extension direction of the web runs in this case in particular perpendicularly to the longitudinal axis. However, it is equally possible that the extension direction of the at least one web can run parallel to the longitudinal axis of the marker. Said edge portions also run on either side of the section or of the web preferably along the longitudinal axis, in particular parallel to the longitudinal axis of the region/x-ray marker. However, the present proposal also includes the situation in which said edge portions can also be introduced at another point.

In particular, the region or x-ray marker can have an oval or elongate form with rounded edges. Due to such an areal increase of the dimensions of the region/x-ray marker in the x- and y-direction of the x-ray marker (z corresponds to the thickness direction), it is possible to replace the double marker used in the case of the present scaffolds with an individual marker. The advantage here lies in particular in the omission of the web separating the two individual markers. Approximately 22% x-ray marker surface is gained as a result.

Further, the region or the x-ray marker is formed as a continuous layer which does not contain any holes or other cut-outs within the continuous layer. Holes or other forms of cut-outs within the continuous layer would result of course in material loss and thereby in decrease of the x-ray visibility. Moreover, a solid marker element as described herein also exhibits an improved x-ray visibility in comparison to discontinuous marker materials such as powders or porous materials.

Provision is also made in accordance with a preferred embodiment of the method according to the invention so that the material layer with the pre-cut region is contacted by an acid, in particular is immersed in an acid, such that a burr produced in the region during the pre-cutting preferably disintegrates on account of the chemical attack of the acid and is thus removed. Here, it is particularly advantageous when the acid has an oxidising effect. Here, the term acid also includes a mixture of a number of acids or also a diluted acid or an acid in an organic solvent. In addition, by means of the selection of oxidising or non-oxidising acids, the material attack can be extended to the oxidised boundary layer provided, or (in an oxidising manner) additionally to the substrate there below.

The reduction or in the best case scenario removal of the burr has the advantage of minimising the risk that material contact with the scaffold can be produced more easily after the assembly due to protruding parts of the burr.

By contacting the material layer with the acid, in particular the cut gap is widened and/or said width of the web is reduced (for example from approximately 8 μm to approximately 3 μm).

The composition of the used acid or acid mixture is dependent in particular on the material of the x-ray marker. With use of pure tantalum an acid mixture consisting of 80 volume % concentrated $HNO_3$ and 20 volume % concentrated HF can be used. In the case of gold, a mixture of concentrated hydrochloric acid and concentrated nitric acid in a ratio of 3:1 is used. The same acid mixture is also used in the case of tungsten and platinum, wherein this has to be heated to temperatures between 60 and 80° C. in order to produce material abrasions in the above-mentioned scope within a period from a few minutes to hours.

In accordance with a preferred embodiment of the method according to the invention, provision is made so that the material layer treated with the acid together with the pre-cut region is rinsed, primarily with water, in order to remove acid residues.

In accordance with a preferred embodiment of the method according to the invention, provision is also made so that the material layer together with the region fixed thereto is oxidised in order to generate a passivation of a surface of the region or x-ray marker. The oxidation is preferably carried out until the web, as predetermined breaking point has, been oxidised through over the entire diameter, such that the web, after the oxidation, consists exclusively of oxidised material and no longer of metal or a metal alloy.

Provision is also made in accordance with a preferred embodiment of the method according to the invention so that, during the oxidation, the predetermined breaking point is severed by being oxidised through completely, and the former integral bond is no longer sufficient to hold the region or x-ray marker at the web. Following complete oxidation of the web, possibly also electrochemical oxidation, and once the x-ray marker has broken off from the material layer, the x-ray marker can be captured and filtered off by a suitable means, for example a vessel encased by mesh.

As a result of this preferred embodiment, a very economical method is achieved, because two method steps can be carried out simultaneously. On the one hand, the x-ray marker is provided with a fixedly adhering and cohesive passivation layer, which provides an insulation of the x-ray marker with respect to corrosion-accelerating local elements. Furthermore, the corrosion of the web means that the predetermined breaking point is weakened to such an extent that the x-ray marker can be easily broken off from the material layer. In particular, the present method, by means of a suitable choice of the web width, provides the possibility to carry out the method in a self-regulating manner. Here, self-regulating is understood to mean that the complete oxidation of the web can define a maximum oxidation time. The oxidation period can thus be determined as well by the thickness of the web. By suitable selection of the web width, the web can be oxidised through and can separate from the material layer at a moment in time when the oxidation layer to be formed has an ideal and advantageous thickness on the x-ray marker. An optimal oxidation thickness layer can thus be regulated by the web width.

Alternatively, there is the possibility to continue the oxidation of the x-ray marker only until the predetermined breaking point still has a minimal integral bond to the rest of the x-ray marker. In this embodiment the predetermined breaking point is severed during or after rinsing processes in distilled water, under the action of a mechanical stimulus, such as ultrasound, and the marker, which is then separated, falls onto the base of the rinsing vessel, from which it can then be easily removed, for example by being filtered off. Other stimuli can consist in swinging, rinsing out, or rinsing off.

The complete or approximately complete oxidation of the at least one web described herein in particular has the advantage that no further mechanical or other steps, such as breaking out or renewed laser cutting, have to be carried out in order to separate the x-ray marker from the material layer. It is also highly advantageous that, by means of the method proposed herein, an x-ray marker which has a uniform, completely cohesive, passivated surface can be provided in an automatic production process. When breaking out or cutting off an x-ray marker from a corresponding material layer, the x-ray marker might have bare metal at the breaking or cutting point on the outer side, and the passivation layer might potentially be provided with scratches, which also expose bare metal. A point with bare metal would have the significant disadvantage that local elements can form much more easily at such a point following application of the x-ray marker to an implant and can promote corrosion of the implant and can significantly reduce the service life of the implant. However, as a result of the method according to the invention, an x-ray marker is provided which has no such points with bare metal. In addition, a uniform x-ray marker of this type can be produced automatically in high numbers during a single process step.

In accordance with a preferred embodiment of the method according to the invention provision is also made so that the oxidation of the surface of the material layer and of the region/x-ray marker is performed plasma-chemically in an electrolyte.

In accordance with a preferred embodiment of the method according to the invention, provision is also made so that the x-ray marker is rinsed (for example with distilled water) after the oxidation in order to remove the electrolyte.

Alternatively, for passivation of the surface of the region or x-ray marker by plasma-chemical treatment, primarily in electrolyte, the surface can be contacted with an aqueous silicate mixture in order to produce an electrically insulating layer on the surface, wherein said layer comprises sodium silicate of the composition $M_2O \cdot n\ SiO_2$ with n=1 to 4, wherein M here can be Na, K or Li. Alternatively, other anionic mixtures can also be used, such as carbonate, sulphate, or phosphate mixtures, primarily with calcium as cation. This method step is preferably performed at increased temperature in order to achieve a sufficient passivation. In one embodiment the passivation step is performed at temperatures of from 30 to 80° C. and preferably at temperatures ranging from 40 to 60° C.

In a further variant, a passivation layer can also be achieved by gas-phase deposition of dielectric materials, such as $SiO_2$.

A further alternative lies in the use and application of coatings having a high barrier effect. By way of example, diamond-like carbon (DLC), SiC or TiN can be applied. Routine methods are known to a person skilled in the art. In addition, a coating with parylene (preferably parylene C), which is a plastic with high barrier effect to aqueous media, primarily as a complete layer, is advantageous. This material can be applied to the substrate as pore-free and transparent polymer film in a vacuum by condensation from the gas phase. A separation of the x-ray marker from the material layer is achieved in this embodiment by a suitable mechanical stimulus, such as ultrasound.

After this, the predetermined breaking point is preferably severed by the action of a force, in particular a periodic force, and therefore the region/x-ray marker is separated from the part of the material layer surrounding the region. In particular, ultrasonic waves can be used for this purpose, which are coupled into the predetermined breaking point.

The plasma-chemical oxidation can be performed in an electrolyte for example, in that the material layer is contacted with a metal conductor (for example titanium wire) and is immersed in an electrolyte, which for example comprises a mineral acid and ethanol, wherein an electrode acting as cathode made of a preferably rust- and acid-resistant metal (for example a suitable rust- and acid-resistant steel) is arranged in the electrolyte or in an electrolyte container receiving the electrolyte. In this plasma-chemical process, an x-ray marker surface is oxidised in particular up to a depth of approximately 2 to 4 µm. Insulating oxide layers can already be arrived from a depth of 0,5 µm on. This (process carried out under plasma-chemical conditions) in particular also causes the oxidation of the predetermined breaking point itself, so that this is preferably oxidised through once the plasma-chemical process is complete. A loss of the material cohesion and a breaking-off of the x-ray marker from the connection to the material layer or from the foil or tube composite result. The separated x-ray marker is then captured, for example by means of a (in particular net-like) capturing device made of plastic, which was placed beforehand in the electrolyte or in the container.

The x-ray marker is then removed from the electrolyte and rinsed. Once the rinsing process (for example in distilled water) is complete, a surface-passivated x-ray marker free from electrolyte residues is present, which can then be fixed to a medical implant (see below as well) once dried (for example in warm air).

Alternatively to the through-oxidation when the plasma-chemical oxidation process is complete, the x-ray marker can also remain in the foil/tube connection once the plasma-chemical process is finished. Separation then occurs only with rinsing in distilled water in a container into which ultrasonic waves for example are coupled. Here, it must be ensured that the ultrasonic influence is dosed so that there is no damage caused to the layer. Other mechanical stimuli specified herein can be suitable, equally.

This procedure on the one hand advantageously rules out mechanical damage to the x-ray marker surfaces and on the other hand leads to a negligibly small remaining metal fracture area of the predetermined breaking point. This remaining fracture area is advantageously significantly smaller than one that would have been produced by mechanical break-off, for example by bending. In addition, the predetermined breaking point is placed inside the x-ray marker. This rules out direct contact with the eyelet.

Due to the use of a material layer, the method advantageously allows a parallelisation of the x-ray marker production.

In accordance with a further preferred embodiment of the method according to the invention, provision is made so that a plurality of regions in the material layer are pre-cut, wherein the regions each form an x-ray marker to be produced.

In accordance with a preferred embodiment of the method according to the invention, the individual regions can then be treated in the manner described herein simultaneously, such that, at the end of the process, a corresponding multiplicity of x-ray markers is produced (simultaneously).

A further aspect of the present invention relates to an x-ray marker which has been produced by the method according to the invention.

A further aspect of the present invention also relates to an x-ray marker which has at least one section which is arranged such that a contact face has a breaking point severed in order to produce the x-ray marker or has a breaking point produced by severing at least one predetermined breaking point, which breaking point is arranged in the section of the x-ray marker such that the breaking point lies further inward (i.e. is disposed closer to the centre of the x-ray marker) than two outer edge portions of the region, between which the section lies (see also above). Further, such x-ray marker may be provided with an insulating layer, preferably a layer of at least one oxide or silicate of the material the material layer is formed of In one embodiment the oxide or silicate layer has a thickness of more than 0.5 µm. In a preferred embodiment the oxide or silicate layer has a thickness in the range of 1 to 8 µm, and more preferably in the range of 2 to 5 µm.

A further aspect of the present invention also relates to a semifinished product for producing an x-ray marker, in particular an x-ray marker according to the invention, wherein the semifinished product is formed by the material layer, in particular in the form of a metal foil or a tube (see also above), into which at least one region of the material layer forming the x-ray marker to be produced is pre-cut such that said region is connected to the part of the material layer surrounding the region (in particular merely) via at least one web extended along an extension direction, which web the forms a predetermined breaking point. The at least one predetermined breaking point is preferably arranged in an section (formed in particular by the pre-cutting) of the region such that the predetermined breaking point lies further inwardly in the extension direction of the web than two edge portions of the region, between which the section lies.

The material layer is preferably formed here such that the web width perpendicularly to the extension direction of the web lies in the range of from 1 µm to 20 µm and preferably in the range of from 2 to 10 µm and in particular in the range of 5 to 7 µm.

The predetermined breaking point is also formed in particular such that in acid medium it corrodes through much more quickly than the other material layer. In keeping the web in the above defined ranges and having the web connected to the x-ray marker located inwardly and directed to the centre of the marker element as suggested herein the herein suggested method for producing x-ray markers for scaffolds is highly advantageously influenced, because the production can be carried out extremely efficient. Not only is it possible that a great number of x-ray markers can be processed simultaneously while still being connected via the web to the material layer after cutting, it is moreover possible to completely passivate the x-ray markers, polish the x-ray markers and disconnect the x-ray markers from the material layer in one step. In comparison to common procedures where the marker disconnection from a material layer is done by another cutting step, the x-ray markers would still be provided with an open spot exhibiting fresh and open marker material which needs to be insulated in order to avoid local elements which highly influence the performance of the x-ray marker and the scaffold. Hence, it is thereby provided a very elegant production procedure x-ray markers for scaffolds facilitated by the specific embodiments of the marker elements themselves and the semifinished product as suggested herein.

In accordance with one embodiment of the semifinished product, provision is preferably made so that a plurality of regions are pre-cut into the material layer, wherein the regions each form an x-ray marker to be produced. The regions can again be connected individually in the above-described manner to the corresponding surrounding part of the material layer, in each case via at least one web.

A semifinished product of this type makes it possible advantageously to produce a plurality of x-ray markers in parallel.

A further aspect of the present invention lastly relates to a medical implant, in particular in the form of a framework, wherein the medical implant comprises at least one x-ray marker according to the invention, which in particular is arranged in a receptacle (what is known as an eyelet) of the framework. A receptacle of this type can be formed for example on a strut of the framework.

By means of the at least one x-ray marker, it is possible to determine the position of the implanted implant by means of radiography, for example in the body of the patient.

The framework is preferably a stent framework, in particular a degradable stent framework, which for example is designed and provided to be implanted into a blood vessel of the patient. Here, the stent framework has a multiplicity of interconnected struts, which form the cells of the stent framework.

Here, the stent framework in particular has two ends, which surround an inlet opening and outlet opening of the stent framework, through which, respectively, blood can flow into and out again from an interior of the stent framework surrounded by the stent framework.

At least at one of the two ends, a receptacle (eyelet) can be provided, which is preferably formed as a through-opening of a strut of the framework or stent framework, wherein an x-ray marker according to the invention is fixed in the receptacle. At the other end, a receptacle can also be provided which is preferably formed as a through-opening of a strut of the framework or stent framework, wherein an x-ray marker according to the invention can likewise be fixed in the receptacle of the other end.

The invention, in an advantageous manner, enables the use of solid x-ray markers, the use of which previously with degradable scaffold materials, such as magnesium or magnesium alloys, would have resulted in increased corrosion rates and therefore in a significantly reduced service life.

The process of laser cutting a large number of markers from a material layer/foil/tube is very economical in terms of production compared to the production of individual markers, since all measures for individual contacting are spared.

The passivation of entire material layer portions/foil/tube portions having pre-cut x-ray markers facilitates the process steps of pickling and passivation by advantages brought about on account of the omission of the individual contacting.

There are no disadvantages, for example as occur in the case of the coating of bulk material, where both adhesion and clumping of the passivation layers with one another and effects resulting from particle abrasion can occur.

The inward predetermined breaking point ensures that there is no metal-metal contact, which promotes local element formation and thus increases the risk of corrosion.

The detachment of the x-ray marker from the material layers or foil/tube composite caused by the process of plasma-chemical or wet-chemical oxidation is not accompanied by any mechanical loading of the predetermined breaking point. The remaining metal fracture area still present at the predetermined breaking point is thus minimised advantageously to a few $\mu m^2$, if there is any such remaining area at all. Even if there was remaining a metal fracture area local elements would not occur due to the inwardly directed position of the area which excludes direct contact between the metal fracture area and the scaffold material.

In addition, the method according to the invention avoids damage to the passivated surface caused by scratches or the like, particularly in the edge regions of the marker, which are particularly susceptible to the formation of local elements, and cannot be ruled out when the markers are pushed out mechanically.

Lastly, when assembling the x-ray markers in non-degradable and insufficiently radiopaque scaffold materials, such as nitinol, complex multi-stage process steps afflicted by high rejection rates (as in the case of galvanic deposition methods for example) are spared.

BRIEF DESCRIPTION OF THE SEVERAL VIEWS OF THE DRAWING

Further features and advantages of the invention will be explained in the description of the drawings of exemplary embodiments of the invention, provided with reference to the drawings, in which.

DESCRIPTION OF THE INVENTION

Figure 2A:
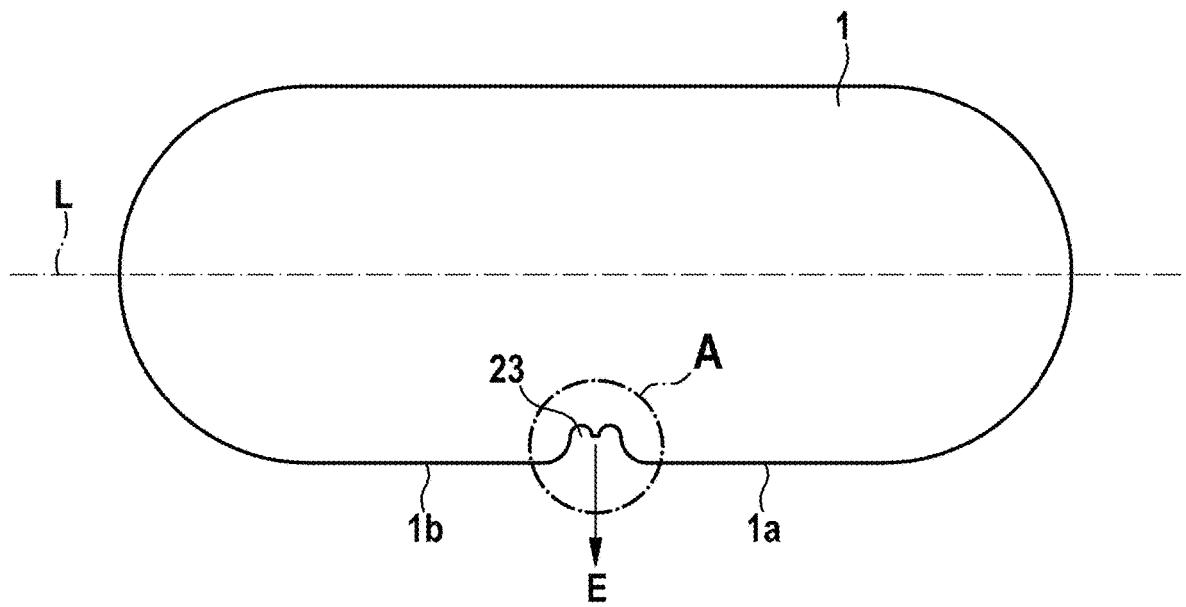
FIG. 2a shows a plan view of an x-ray marker according to the invention having a predetermined breaking point.
Figure 2B:
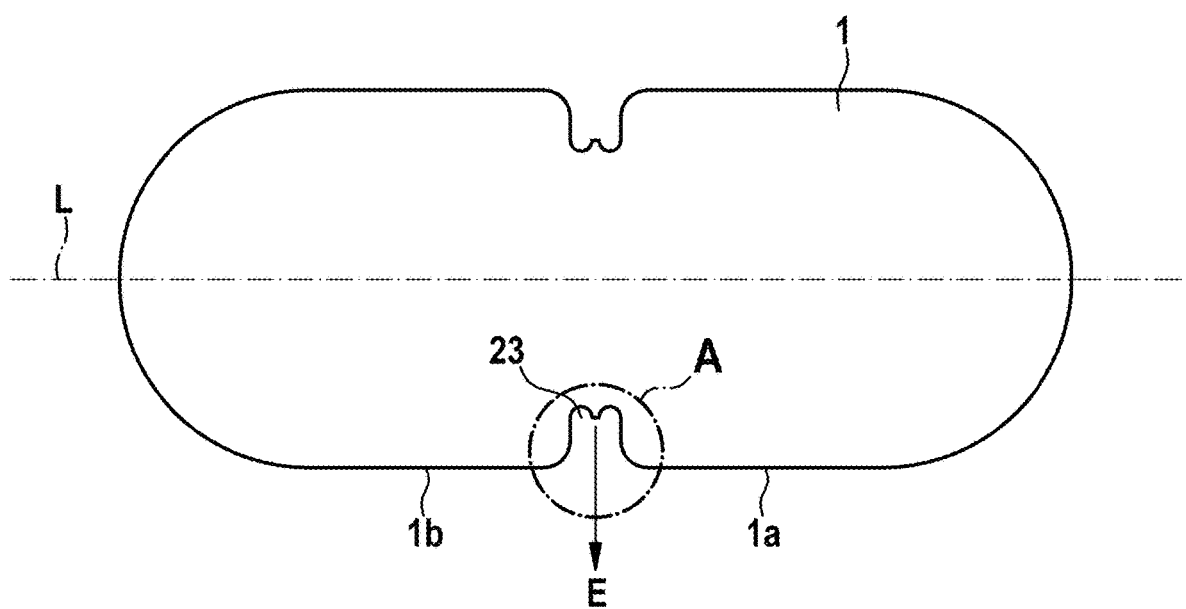
FIG. 2b shows a plan view of an x-ray marker according to the invention having two predetermined breaking points.
Figure 3:
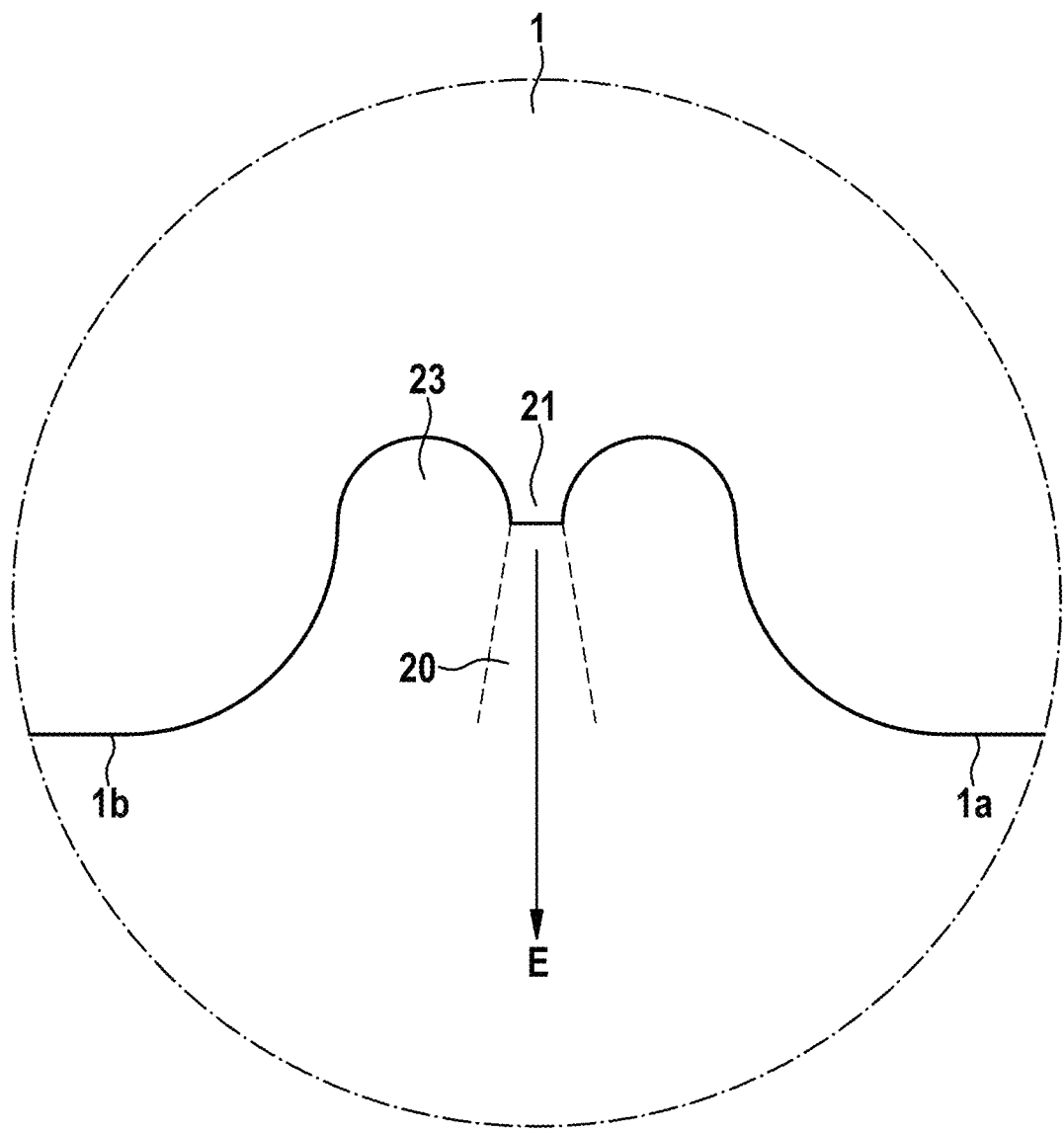
FIG. 3 shows the detail A from FIG. 2.

FIGS. 1 to 3 show an x-ray marker 1 according to the invention which preferably comprises a highly absorbent x-ray marker surface (for example made of tungsten and/or tantalum), which preferably is passivated so that, following assembly in the receptacles (eyelets) 101 (FIG. 4) of a degradable or also non-degradable medical implant 100 (for example a framework, in particular a stent framework), there is no occurrence of accelerated corrosion.

Figure 1A:
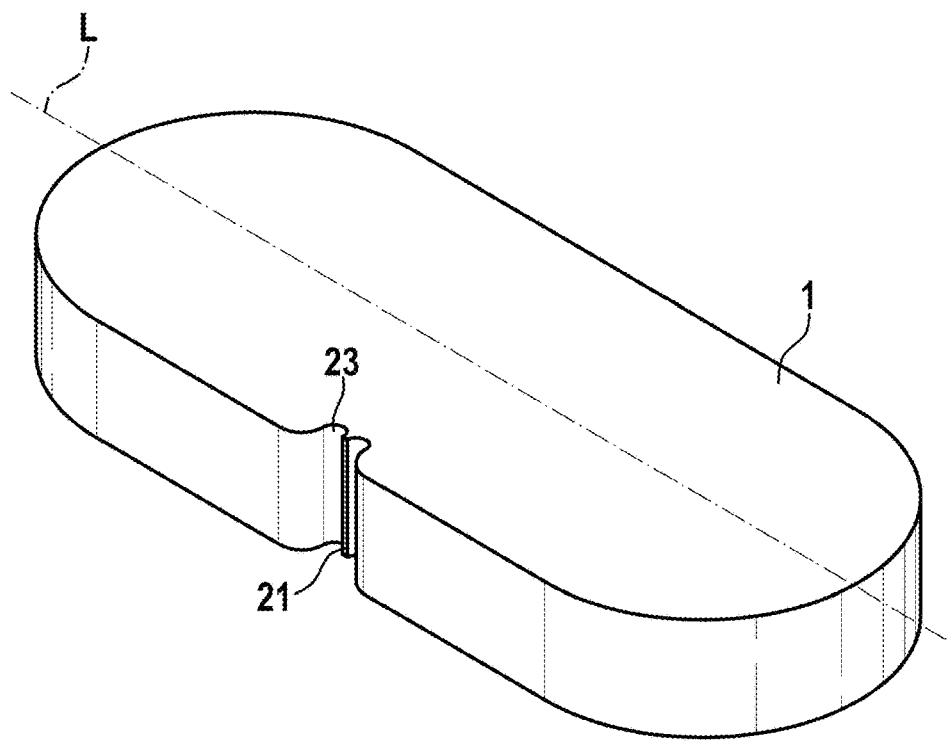
FIG. 1a shows a perspective view of an x-ray marker according to the invention having a predetermined breaking point.
Figure 1B:
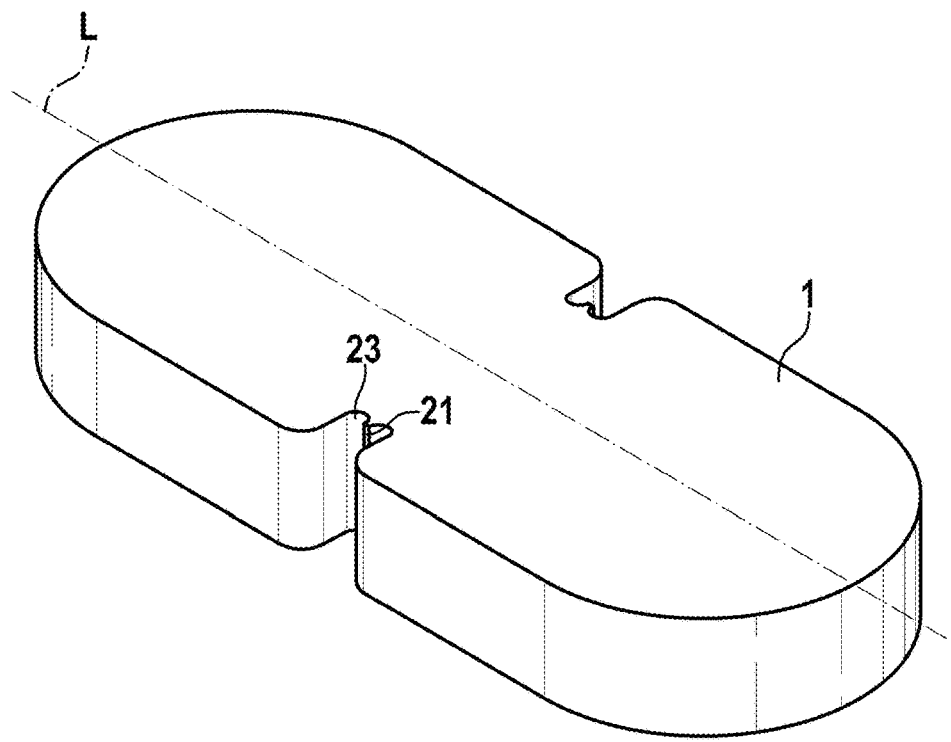
FIG. 1b shows a perspective view of an x-ray marker according to the invention having two predetermined breaking points.

In particular, FIG. 1*a* shows a graphical representation of an x-ray marker 1 according to the invention which extends along the longitudinal direction L and comprises a section 21 in which the predetermined breaking point 23 is disposed inwardly. In the illustration of FIG. 1*b*, an embodiment of the x-ray marker 1 according to the invention which has two mutually opposed sections 23 is shown in the same illustration.

FIGS. 2*a* and 2*b* now show the x-ray markers 1 from FIGS. 1*a* and 1*b* in a plan view. In both illustrations a region A is marked by a circle and is shown in detail in FIG. 3. By way of example, dimensions here in FIGS. 2*a* and 2*b* are specified in millimetres and standard deviations thereof.

FIG. 3 shows a detailed view of the region A from FIGS. 2*a* and 2*b*. What can be seen is the position of the predetermined breaking point 21 in the section 23 directed inwardly from the outer side of the x-ray marker 1. The inwardly directed position is visible in particular by the edges 1*a* and 1*b* arranged further outwardly in the extension direction E compared to the predetermined breaking point 21. The web 20 provided formerly is indicated in FIG. 3 by dashed lines.

Figure 4A:
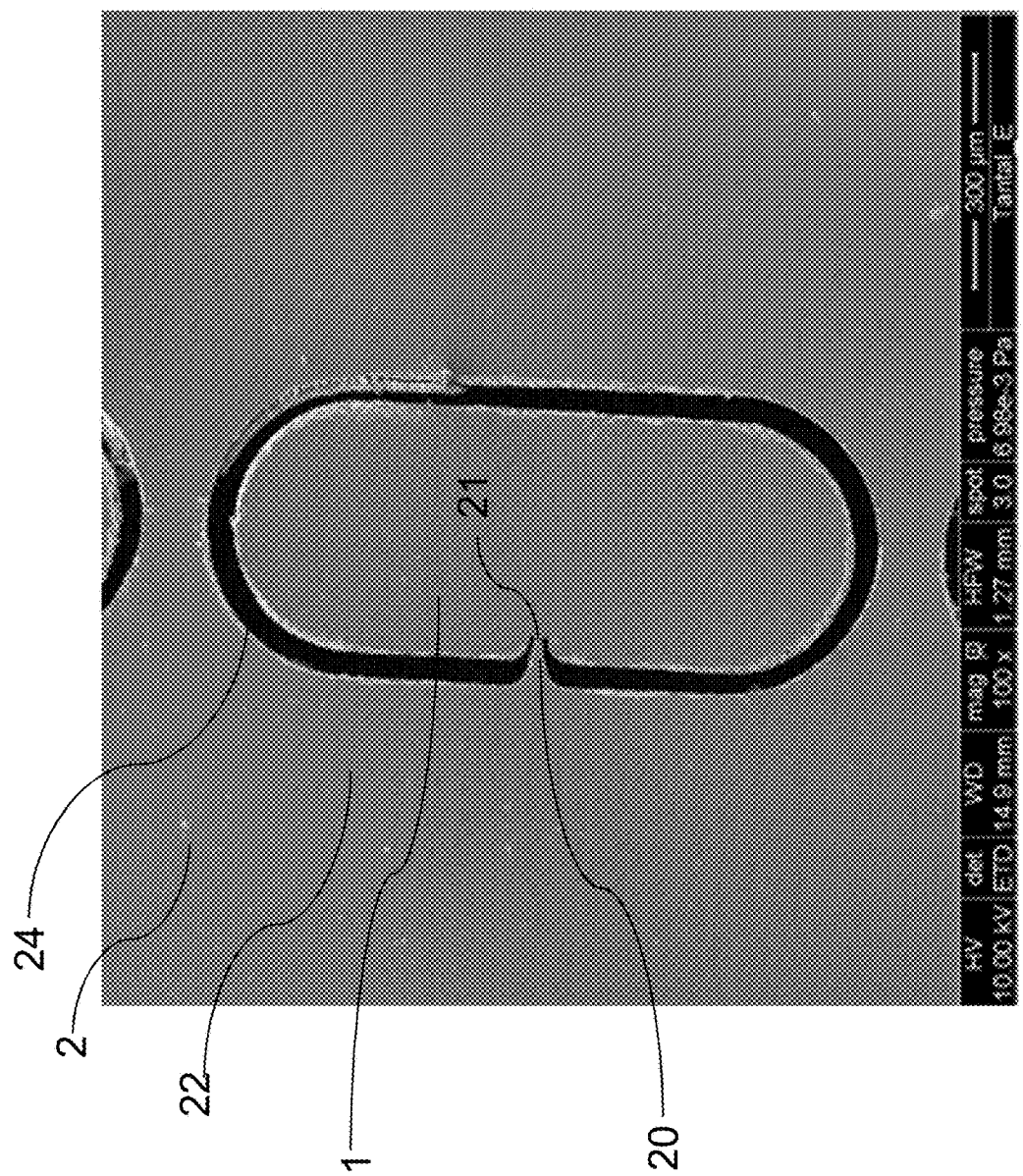
FIG. 4a shows an image recorded by scanning electron microscope (SEM) of the x-ray marker still in the material layer or foil material and connected to the material layer via a web.
Figure 4B:
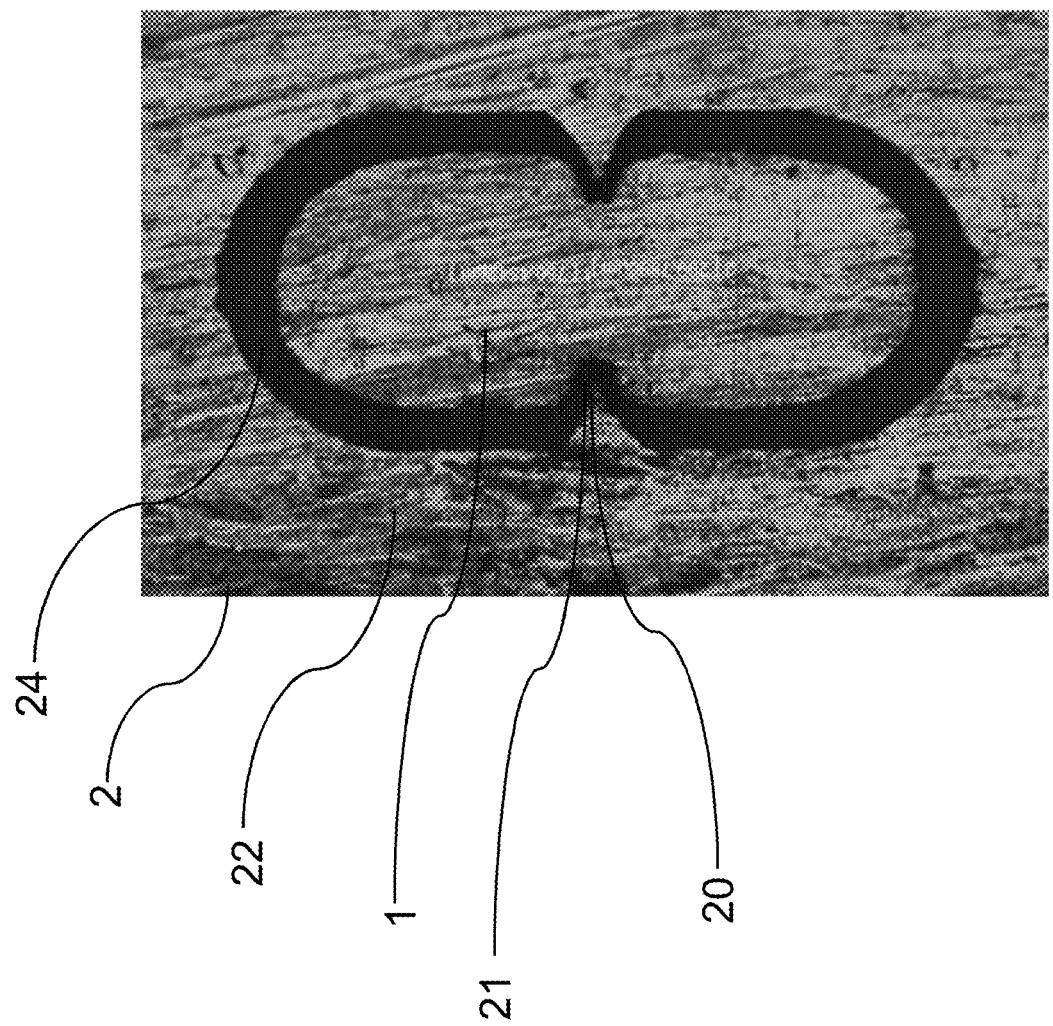
FIG. 4b shows an image recorded by light microscope of the x-ray marker still in the material layer or foil material and connected to the material layer via two webs.

This specific arrangement according to the invention is also visible in FIGS. 4*a* and 4*b*, which show microscopic images of the x-ray marker 1 connected to the material layer 2 via one web (FIG. 4*a*) or two webs (FIG. 4*b*). The gap 24 here separates the x-ray marker 1 from the surrounding material 22 of the material layer 2.

Figure 5:
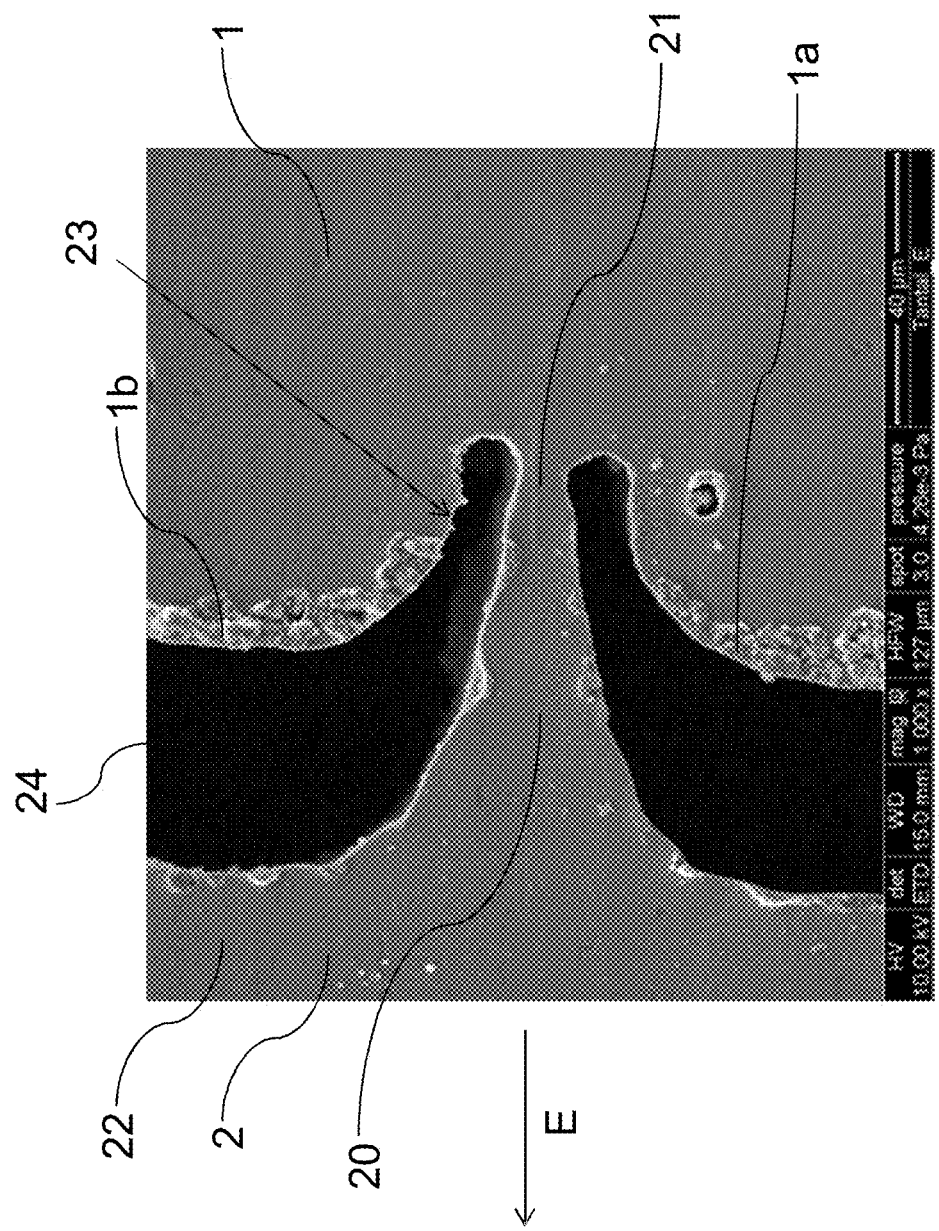
FIG. 5 shows a detailed view, obtained by scanning electron microscope, of an inwardly offset predetermined breaking point that is still intact.

In FIG. 5, an image of the region A of FIGS. 2*a* and 2*b* recorded by SEM is shown, wherein here the web 20 is still connected to the x-ray marker 1 via the predetermined breaking point 21. The inwardly directed position of the predetermined breaking point 21 compared with 1*a* and 1*b* is also clearly visible here.

Figure 6:
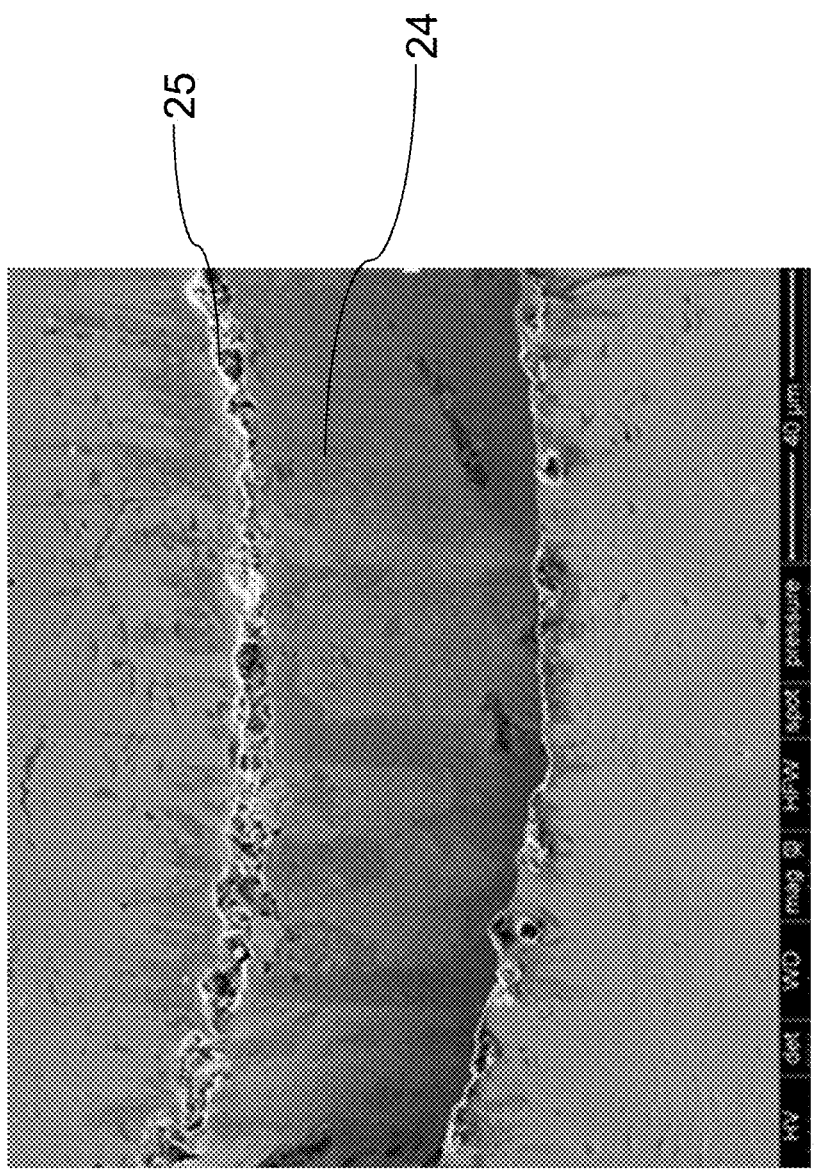
FIG. 6 shows burr formation at the laser-cutting edges: SEM image before the pickling process, i.e. before contact of the material layer with a suitable acid.
Figure 7:
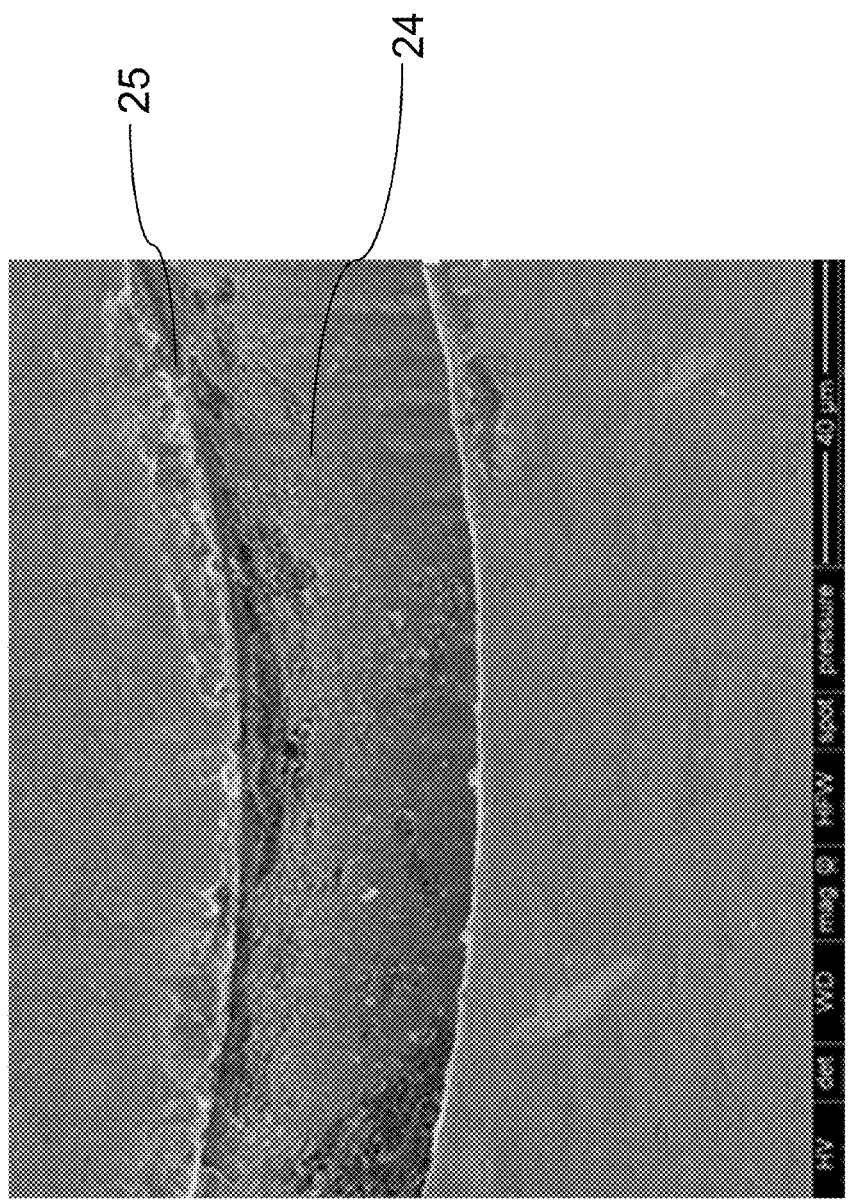
FIG. 7 shows the burr formation at the laser-cutting edges: SEM image after the pickling process.

FIG. 6 shows an image of the gap 24 recorded by SEM. At the cutting edge, the burr 25 can be seen before this is treated with suitable acid. By way of comparison, the effects of the treatment with a suitable acid on the gap 24 and the burr 25 are shown in FIG. 7. By way of comparison it can be seen that the burr 25 has significantly lost roughness and sharp edges, and the treatment with suitable acid results in a material-removing effect.

Figure 8:
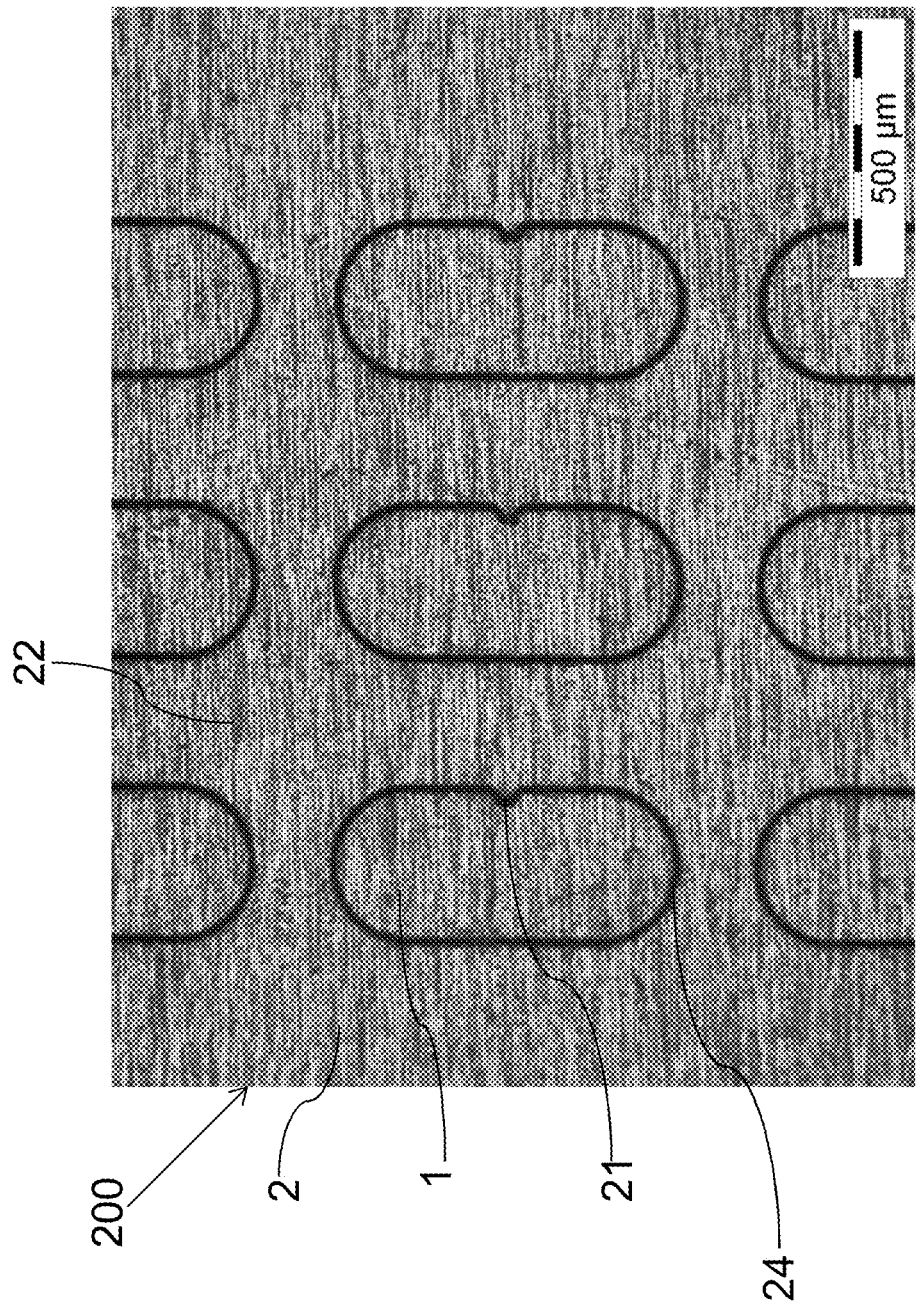
FIG. 8 shows an overview of laser-cut x-ray markers in a semifinished product, each marker having an inward predetermined breaking point.

FIG. 8 also shows that the present method is suitable for pre-cutting a multiplicity of x-ray markers 1 into a material layer 2 so as to achieve a high level of automation of the production process. It can be seen that a multiplicity of x-ray markers 1 can be produced simultaneously by the same applied method step.

Figure 9:
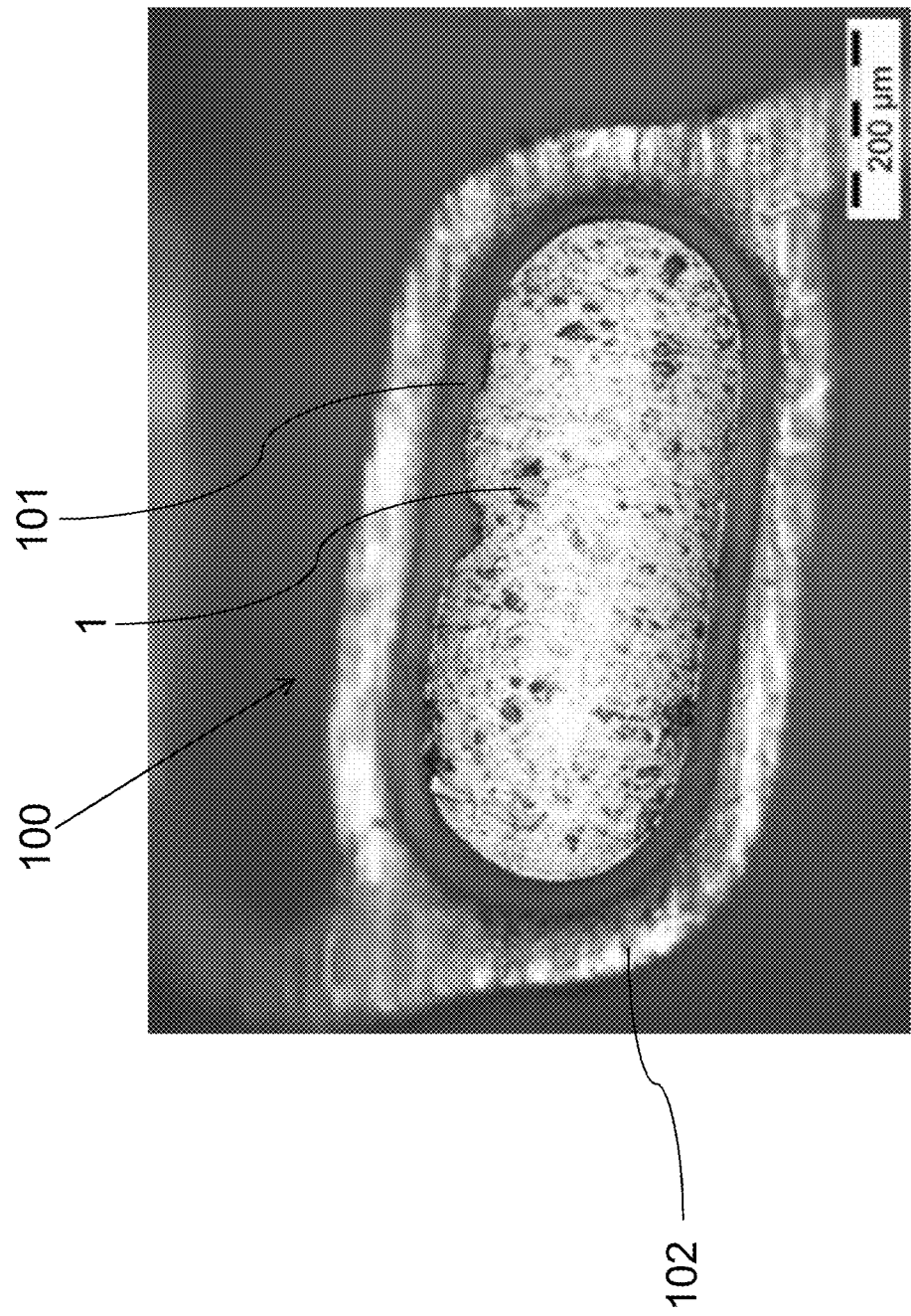
FIG. 9 shows an eyelet with, stuck therein, an x-ray marker according to the invention having an inward predetermined breaking point (image recorded by light microscope).

FIG. 9 shows an image recorded by light microscope of an x-ray marker 1 according to the invention which has been introduced into a receptacle 101 (eyelet) of a strut 102 of a framework 100. In this illustration it can be clearly seen that any metal-metal contact with the strut 102 is ruled out by the inwardly directed position of the predetermined breaking point.

The x-ray marker 1 is preferably produced in that a corresponding region 1 is pre-cut almost fully into a flat material layer 2, which is preferably a metal foil 2, for example by means of a laser (for example see FIG. 4*a*, 4*b* or 8).

In order to prevent a premature breaking-off of the markers 1 from the material layer 2, these are provided with at least one geometrically inwardly offset predetermined breaking point 21, as is illustrated for example in FIGS. 1 to 3 and 5.

Alternatively to a single predetermined breaking point, an embodiment is shown by way of example in FIGS. 1*b*, 2*b* and 4*b*, in which a second predetermined breaking point opposite the first predetermined breaking point is provided.

Said pre-cutting is carried out in particular so that the region 1 of the material layer 2 is connected via at least one web 20, which is extended along an extension direction E and which forms the (inward) predetermined breaking point 21, to a part 22 of the material layer 2 surrounding the region 1, wherein the predetermined breaking point 21 is "inward", since it is arranged in a section 23 (formed by the pre-cutting) which is formed or arranged at an outer edge of the region 1 so that the predetermined breaking point 21 or the base of the web 20 lies further inwardly in the extension direction E (for example FIGS. 2*a*, 2*b* and 5) of the web 20 (i.e. closer to the centre of the region/x-ray marker 1) than two edge portions 1*a*, 1*b* of the region 1, between which the section 23 is disposed.

As can be seen in particular from FIGS. 2*a*, 2*b* and 3, provision can be made so that the region 1 or the x-ray marker 1 is formed in an elongate manner and extends along a longitudinal axis L. Said extension direction E of the web 20 runs here primarily perpendicularly to the longitudinal axis L. Furthermore, said edge portions 1*a*, 1*b* run on either side of the section 23 or web 20, preferably along or parallel to the longitudinal axis L of the region 1/x-ray marker 1. In particular, the region 1 or x-ray marker 1 can have an oval or elongate form with rounded corners or semi-circular ends.

The web width B of the predetermined breaking point 21 or of the web 20 (see FIGS. 3 and 5) is for example approximately 8 μm. The gap 24 (in particular laser cutting gap 24), which is produced during the pre-cutting, is for example between 10 and 100 μm wide. The mechanical strength of the predetermined breaking point 21 is sufficient to attain an adequate transport and storage capability without the marker 1 breaking off prematurely.

In a subsequent process, the film or material layer 2 is immersed in a suitable acid or acid mixture. The composition of this acid mixture is dependent, as described herein, on the material of the x-ray marker 1. The pickling effect that then occurs results in a chemical levelling or polishing of the very rough burr 25 (see FIGS. 6 and 7) produced during the pre-cutting or laser cutting, and in particular results in a small widening of the laser cutting gap 24. The web width B is reduced in such a step for example from approximately 8 μm to approximately 3 μm. After an intermediate—preferably two-stage—rinsing process, the foil/material layer 2 is contacted by way of example with a titanium wire and is immersed in a mixture of an electrolyte containing mineral acid and ethanol. The electrolyte container here has an electrode configured as a cathode and made of a rust- and acid-resistant steel.

A plasma-chemical process is performed, which is described by way of example in some examples of the invention detailed further below, wherein, during the course of said process, the x-ray marker surface is oxidised or otherwise passivated, for example to a depth of approximately 2 to 4 µm. This (process (oxidation) preferably carried out under plasma-chemical conditions) at the same time also causes an oxidation of the predetermined breaking point 21 itself. This is preferably oxidised through once the plasma-chemical process is complete. A corresponding loss of the material cohesion and a breaking-off of the marker 1 from the connection of the foil or the material layer 2 results. The separated marker 1 now falls into a capturing device, which for example is net-like (for example made of a plastic), which was placed beforehand in the electrolyte. The device is then removed from the electrolyte and rinsed preferably a number of times. Once the rinsing process is complete (preferably in distilled water), x-ray markers that are free from electrolyte residues and that are surface-passivated are present, which are then available—after drying (for example in warm air)—for the assembly process.

In the method according to the invention, preferably material layers 2 or semifinished products 200 are used, as shown in FIG. 10. Here, a number of regions 1/x-ray markers 1 are pre-cut (in the above-described way) into a material layer 2 (metal foil 2) so that a number of x-ray markers 1 can be produced in parallel.

A finished x-ray marker 1 according to the invention is preferably glued in accordance with FIGS. 6 and 9 into a receptacle (what is known as an eyelet) 101, which for example is formed as a through-opening 101 in a strut 102 of a medical implant 100. An implant 100 of this type is preferably a framework 100, in particular a stent framework 100, which is preferably degradable. The x-ray marker 1 can of course also be used with non-degradable frameworks/stent frameworks 100.

Some detailed examples of the invention will be described hereinafter.

EXAMPLE 1

A framework (scaffold) 100 made of a degradable magnesium alloy (see FIG. 6) has a receptacle (eyelet) at a distal end and at a proximal end, which receptacle is provided for assembly with x-ray markers 1. The diameters of the oval eyelet 101 are approximately 800 µm and approximately 350 µm. Oval undersized solid markers 1 made of tungsten with inward predetermined breaking points 21 are assembled in these eyelets 101 (see FIGS. 1 and 2). The thickness of this tungsten marker 1 is in particular identical to the wall thickness of the scaffold 100, and for example is 100 µm. The undersize relative to the corresponding eyelet dimensions is in each case 20 to 30 µm, for example. The tungsten marker 1 has a predetermined breaking point 21 in relation to the rest of the foil 2 (see FIGS. 3 and 5) and has therefore been cut out beforehand from a foil 2 by means of a laser light beam (see FIGS. 4 and 5). The cutting gap 24 is for example between 10 and 100 µm. The burr 25 produced during the laser cutting is removed by pickling in a mineral acid, for example an acid mixture having a temperature of 30° C. formed from nitric and hydrochloric acid, over 2 to 5 min (see FIGS. 7 and 8). This is followed by a three-stage rinsing process in distilled hot water having a temperature of 80° C.

After being dried in air, the foil material 2 is plasma-chemically oxidised with the laser-cut x-ray markers 1 in an electrolyte containing sulphuric acid and phosphoric acid. The oxidation of the chemically stable element tungsten is brought about by the locally limited plasma discharges at bath voltages above 180 V. Here, individual plasma discharges scan the tungsten surface systematically. The surface of the marker 1 thus obtains a method-typical porous surface, which consists predominantly of $WO_3$, which is electrically non-conductive and is practically insoluble in water. The oxide layer thickness is between 2 and 4 µm. On account of the conversion nature, i.e. the temporarily fused surface produced by the plasma discharges, the original external geometry of the marker 1 is retained and the oxide layer has a high adhesive strength on account of the material bonding to the underlying metal substrate. Since the plasma-chemical oxidation effect is also effective at the predetermined breaking point 21, which is approximately 3 µm wide, said predetermined breaking point is oxidised through. The separated marker 1 falls into a net-like capturing device, which was placed previously in the electrolyte. A subsequent pickling effect in the electrolyte does not take place, since the previously plasma-chemically oxidised surface has a sufficiently high corrosion resistance compared to a maximum residence time in the electrolyte of two minutes. The x-ray marker 1 is then removed from the electrolyte and then subjected to a multi-stage rinsing process in hot water at a temperature of 80° C. Once the rinsing process in distilled water is complete, x-ray markers 1 that are free of electrolyte residues and that are surface-passivated are now provided and are then dried in warm air and are available for assembly processes.

The assembly process, i.e. the connecting of the x-ray marker(s) 1 to the corresponding implant 100 starts with the wetting or immersion of the x-ray marker 1 in a silicone adhesive, for example: NUSIL Med 2. In parallel thereto, the inner sides of the eyelet (see FIG. 6) are wetted with the aid of a thin plastic needle, which has been immersed previously in the silicone adhesive. The x-ray marker 1 is then placed in the eyelet 101 using tweezers or another suitable handling device. Another option is to push the x-ray marker directly from the material layer into the receptacle. The silicone adhesive is then cured in a hot-air oven at 150° C. over a period of time of 15 min. The finished, assembled x-ray marker 1 is illustrated in FIG. 9.

EXAMPLE 2

According to Example 2, the scaffold 100 is provided with an x-ray marker 1 made of tantalum, which has a microporous surface made of tantalum oxide, produced by means of plasma-chemical oxidation.

The scaffold 100 made of a degradable magnesium alloy (see FIG. 6) again has an eyelet 101 at the distal end and at the proximal end, which eyelets are provided for assembly with x-ray markers 1. The diameters of the corresponding oval eyelet 101 are approximately 800 µm and approximately 350 µm. Oval undersized solid markers 1 made of tantalum with inward predetermined breaking points 21 are assembled in these eyelets 101 (see FIGS. 1 and 2). The thickness of this tantalum marker 1 is identical to the wall thickness of the scaffold 100 and for example is 100 µm. The undersize relative to the corresponding eyelet dimensions is in each case 20 to 30 µm. The tantalum marker 1 has a predetermined breaking point 21 in relation to the rest of the foil 2 (see FIGS. 3 and 5) and has therefore been cut out beforehand from a foil 2 by means of a laser light beam (see FIGS. 4 and 5). The cutting gap 24 is between 10 and 100 µm in this case as well.

The burr 25 produced during the laser cutting is removed by pickling in a mixture formed from nitric acid and hydrofluoric acid at room temperature, over 1 to 3 min. This is followed by a three-stage rinsing process in distilled hot water having a temperature of 80° C.

After being dried in air, the foil material 2 is plasma-chemically oxidised with the laser-cut x-ray markers 1 in an electrolyte containing phosphoric acid. The oxidation of the chemically stable element tantalum is brought about by the locally limited plasma discharges at bath voltages above 180 V. Here, individual plasma discharges scan the tantalum surface systematically. The surface of the marker 1 thus obtains a method-typical porous surface, which consists predominantly of $Ta_2O_5$ and Ta phosphates, which are electrically non-conductive. The oxide layer thickness is between 0.5 and 4 µm. On account of the conversion nature of the temporarily melted surface produced by the plasma discharges, the original external geometry of the marker 1 is retained and the oxide layer has a high adhesive strength on account of the material bonding to the underlying metal substrate. Since the plasma-chemical oxidation effect is also effective at the predetermined breaking point 21, which is approximately 3 µm wide, said predetermined breaking point is oxidised through. The separated marker 1 falls into a net-like capturing device, which was placed previously in the electrolyte. A subsequent pickling effect in the electrolyte does not take place, since the previously plasma-chemically oxidised surface has a sufficiently high corrosion resistance compared to a maximum residence time in the electrolyte of a few minutes. The x-ray marker 1 is then removed from the electrolyte and then subjected to a multi-stage rinsing process in hot water at a temperature of 80° C. Once the rinsing process in distilled water is complete, x-ray markers 1 that are free of electrolyte residues and that are surface-passivated are now provided and are then dried in warm air and are available for assembly processes.

The assembly process starts again with the wetting or immersion of the x-ray marker 1 in a silicone adhesive, for example NUSIL Med 2. In parallel thereto, the inner sides of the eyelet 101 (see FIG. 6) are wetted with the aid of a thin plastic needle, which has been immersed previously in the silicone adhesive. The x-ray marker 1 is then placed in the eyelet 101 using tweezers or another suitable handling device. The silicone adhesive is then cured in a hot-air oven at 150° C. over a period of time of 15 min. The finished, assembled x-ray marker 1 is constructed as illustrated in FIG. 9.

EXAMPLE 3

According to Example 3 of the invention, a scaffold 100 made of nitinol is provided with an x-ray marker 1 made of gold having a predetermined breaking point 21 approximately 5 µm wide.

The scaffold 100 made of a nickel-titanium alloy nitinol (see FIG. 6) has an eyelet 101 at the distal end and at the proximal end, which eyelet is provided for assembly with an x-ray marker 1. The diameters of the corresponding oval eyelet 101 are approximately 800 µm and approximately 350 µm. Oval undersized solid markers 1 made of gold with inward predetermined breaking points 21 are assembled in these eyelets 101 (see FIGS. 1 and 2). The thickness of this gold marker 1 is identical to the wall thickness of the scaffold 100 and for example is 100 µm. The undersize relative to the corresponding eyelet dimensions is in each case 20 to 30 µm. The gold marker 1 has a predetermined breaking point 21 in relation to the rest of the foil 2 (see FIGS. 3 and 5) and has therefore been cut out beforehand from a foil 2 by means of a laser light beam (see FIGS. 4 and 5). The cutting gap 24 is between 50 and 100 µm in this case as well.

The burr 25 produced during the laser cutting is removed by pickling diluted aqua regia (1 part $HNO_3$+3 parts HCl). After a treatment time of approximately 1 min., the foil 2 is removed from the pickling bath and is freed of adhering pickling residues in a three-stage rinsing process in distilled hot water having a temperature of 80° C.

The film 2 is then immersed in an aqueous sodium-silicate mixture or lithium-silicate mixture (waterglass). This mixture has a temperature of approximately 50° C. After a treatment time of approximately 5 min., an electrically insulating layer formed of silicates and approximately 2 to 5 µm thick is deposited on the gold surfaces, which for example can have the following empirical formulas, such as $Na_2O_7Si_3$, $Na_2O_3Si$, $Na_2O_5Si_2$ or $Na_4O_4Si$ or in the case of the lithium silicate $Li_2O$, $SiO_2$ or $Li_2SiO_3$. The following two method steps can then be performed:

a) After being dried in air, the foil material 2 with the laser-cut x-ray markers 1 and the dielectric layer now provided is brought into a plastic container filled with distilled water, which container is exposed to ultrasound in the frequency range between 25 and 50 kHz. The x-ray markers 1 are set in mechanical vibration, meaning that they break off at the predetermined breaking point, break off from the connection to the foil, and drop into the vessel, without the surface being damaged. The water is then removed from the plastics container and the separated x-ray markers are dried in air.

b) After being dried in air, the foil material 2 with the laser-cut x-ray markers 1 and the dielectric layer now provided is brought into a slightly alkaline, diluted NaOH solution. The pH value is between 8 and 9. The plastic container with the x-ray markers 1 now coated with sodium silicate is brought into an ultrasonic bath. By applying ultrasound in the frequency range between 25 and 50 kHz, the foil material is set in slight vibration, which causes the individual markers 1 to break off from the connection to the foil 2 at the predetermined breaking point 21. The separated markers 1 can then be removed from the container and dried in air.

By both variations a) and b) plastic deformations as well as surface damages too were avoided.

The assembly process starts again with the wetting or immersion of the x-ray marker 1 in a silicone adhesive, for example NUSIL Med 2. In parallel thereto, the inner sides of the eyelet 101 (see FIG. 6) are wetted with the aid of a thin plastic needle, which has been immersed previously in the silicone adhesive. The x-ray marker 1 is then placed in the eyelet 101 using tweezers or another suitable handling device. The silicone adhesive is then cured in a hot-air oven at 150° C. over a period of time of 15 min. The finished, assembled x-ray marker 1 is again constructed as illustrated in FIG. 9.

The invention claimed is:
1. A method for producing x-ray markers, the method comprising:
   providing a material layer;
   precutting a region of the material layer forming the x-ray marker to be produced, such that the region is connected via at least one web, which forms a predeter- mined breaking point, to a part of the material layer surrounding the region entirely;

the predetermined breaking point being arranged inwardly, closer to a center of the region, than two edge portions of the region adjoining the at least one web; and severing the web at the predetermined breaking point in order to detach the x-ray marker from the part of the material layer surrounding an entirey of the region forming the x-ray marker.

2. The method according to claim 1, wherein the material layer is a metal foil or a metal tube made of radiopaque metal.

3. The method according to claim 1, which comprises precutting a width of the web perpendicularly to an extension direction of the web in a range of from 1 µm to 20 µm.

4. The method according to claim 1, which comprises, during the pre-cutting, producing a gap surrounding the region, the gap having a width ranging from 10 µm to 100 µm.

5. The method according to claim 1, which comprises contacting the material layer together with the pre-cut region with an acid, to reduce a burr that is produced during the pre-cutting at the region.

6. The method according to claim 5, which comprises polishing the pre-cut region with the acid.

7. The method according to claim 5, which comprises rinsing the material layer treated with the acid together with the region formed in the precutting step after the contacting with the acid.

8. The method according to claim 1, which comprises passivating an outer surface of the region connected to the material layer for protection against corrosion, by a measure selected from the group consisting of:

oxidation of the surface;

coating with a dielectric layer;

contacting of the surface with an aqueous silicate mixture for producing an electrically insulating layer on the surface; and application of a complete layer of parylene.

9. The method according to claim 8, wherein:

the oxidation of the surface is a plasma-chemical oxidation carried out in an electrolyte;

the coating with the dielectric layer is a gas-phase deposition producing thin silicon oxide layers;

the electrically insulating layer on the surface comprises sodium silicates.

10. The method according to claim 1, which comprises separating the region, optionally after passivation, from the part of the material layer surrounding the region by one of the following measures:

an oxidation performed for passivation, wherein the predetermined breaking point is fully oxidized and is thus severed; or vibrating the predetermined breaking point until breakage.

11. The method according to claim 10, wherein the vibrating step comprises exposing the predetermined breaking point to ultrasonic waves.

* * * * *